US 6,790,232 B1

(12) United States Patent
Lang (10) Patent No.: US 6,790,232 B1
(45) Date of Patent: Sep. 14, 2004

(54) MULTIFOCAL PHAKIC INTRAOCULAR LENS

(75) Inventor: Alan J. Lang, Long Beach, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/302,977

(22) Filed: Apr. 30, 1999

(51) Int. Cl.$^7$ .................................................. A61F 2/16
(52) U.S. Cl. ...................... 623/6.27; 623/6.28; 623/6.11
(58) Field of Search ................................ 623/6.24, 6.27, 623/6.11, 6.34, 6.23, 6.28, 6.29, 6.3

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |

(List continued on next page.)

FOREIGN PATENT DOCUMENTS

| | | | |
|---|---|---|---|
| AU | 3225789 | 10/1989 | |
| DE | 2702117 | 7/1978 | |
| DE | 2702117 A | * 7/1978 | ............ G02C/7/04 |

(List continued on next page.)

OTHER PUBLICATIONS

Thornton, Color Atlas of Lens Implanation, Accommodation in Pseudophakia, pp. 159–162, 1991.
Menezo, et al. J Cataract Refract Surg 24, Aug. 1998.

(List continued on next page.)

*Primary Examiner*—David J. Isabella
*Assistant Examiner*—Urmi Chattopadhyay
(74) *Attorney, Agent, or Firm*—Stout, Uxa, Buyan & Mullins, LLP; Frank J. Uxa; Peter J. Gluck (57) ABSTRACT

An intraocular lens for use in a mammalian eye having a natural lens, the intraocular lens including a lens body sized and adapted for placement in the eye, and having a baseline optical power and at least one optical add power. The at least one optical add power is reduced relative to the corresponding optical power of a similar intraocular lens adapted for placement in a similar eye in which the natural lens has been removed.

36 Claims, 4 Drawing Sheets

U.S. PATENT DOCUMENTS

| | | |
|---|---|---|
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Neilsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,702,244 A | 10/1987 | Mazzocco |
| 4,704,016 A | 11/1987 | De Carle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,074,877 A | 12/1991 | Nordan |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,236,452 A | 8/1993 | Nordan |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,702,440 A | 12/1997 | Portney |
| 5,766,244 A | 6/1998 | Binder |
| 5,769,890 A | 6/1998 | McDonald |
| 5,776,191 A | 7/1998 | Mazzocco |
| 5,814,103 A | 9/1998 | Lipshitz et al. |
| 5,843,188 A | 12/1998 | McDonald |
| 5,847,802 A * | 12/1998 | Menezes et al. ............ 531/161 |
| 5,864,378 A | 1/1999 | Portney |
| 5,864,379 A * | 1/1999 | Dunn ......................... 351/161 |
| 5,876,442 A | 3/1999 | Lipshitz et al. |
| 5,898,473 A | 4/1999 | Seidner et al. |
| 5,929,969 A | 7/1999 | Roffman |
| 6,013,101 A | 1/2000 | Israel |
| 6,096,078 A | 8/2000 | McDonald |
| 6,110,202 A * | 8/2000 | Barraquer et al. ......... 623/6.43 |
| 6,176,878 B1 | 1/2001 | Gwon et al. |
| 6,197,058 B1 * | 3/2001 | Portney ..................... 623/6.34 |
| 6,217,612 B1 | 4/2001 | Woods |
| 6,231,603 B1 | 5/2001 | Lang et al. |
| 6,457,826 B1 * | 10/2002 | Lett ........................... 351/161 |

FOREIGN PATENT DOCUMENTS

| | | | |
|---|---|---|---|
| DE | 3246306 | 6/1984 | |
| DE | 3246306 A1 * | 6/1984 | ............ G02C/7/04 |
| EP | 939016 | 10/1963 | |
| EP | 0246216 | 11/1987 | |
| EP | 0329981 | 8/1989 | |
| EP | 0337390 | 10/1989 | |
| EP | 0342895 | 11/1989 | |
| EP | 0351471 | 1/1990 | |
| EP | 0480748 | 4/1992 | |
| EP | 0566170 | 10/1993 | |
| EP | 0691109 | 1/1996 | |
| EP | 0780718 | 6/1997 | |
| EP | 0897702 | 2/1999 | |
| FR | 2666735 | 3/1992 | |
| FR | 0488835 | 6/1992 | |
| GB | 2124500 | 2/1984 | |
| GB | 2129155 | 5/1984 | |
| GB | 2146791 | 4/1985 | |
| GB | 2192291 | 1/1988 | |
| GB | 2215076 | 9/1989 | |
| IL | 2058391 | 4/1981 | |
| WO | 8603961 | 7/1986 | |
| WO | 8700299 | 1/1987 | |
| WO | 8707496 | 12/1987 | |
| WO | 8902251 | 3/1989 | |
| WO | 8911672 | 11/1989 | |
| WO | 91/09336 | 6/1991 | |

| WO | 94/16648 | 8/1994 |
| WO | 95/03783 | 2/1995 |
| WO | 9610968 | 4/1996 |
| WO | 96/15734 | 5/1996 |
| WO | 96/25126 | 8/1996 |
| WO | 97/12272 | 4/1997 |
| WO | 97/43984 | 11/1997 |
| WO | 98/21621 | 5/1998 |
| WO | 98/49594 | 11/1998 |
| WO | 9856315 | 12/1998 |
| WO | 00/46629 | 8/2000 |
| WO | 00/66039 | 11/2000 |
| WO | 01/34067 | 5/2001 |

OTHER PUBLICATIONS

Fechner, et al. J Cataract Refract Surg 24, Jan. 1998.
World Optics Inc. Ophthalmology Times, Mar. 15, 1995.
Lolab Corp, Ophthalmology Times, Mar. 15, 1995.
Universe IOL Center, Ocular Surgery News Int'l, no Date Given.
Hanita Lenses, Ocular Surgery News Int'l, no Date Given.
Alcon Surgical, Alcon Laboratories, no Date Given.
Mediphacos Ltda. Ocular Surgery News, Int'l, no Date Given.
Storz Ophthalmics, Inc, Model L122UV ACL, no Date Given.
Opthalmed Inc, OMAC–260, no Date Given.
Chauvin–Opsia, Azurite ACL (0459) no Date Given.
AMO Specs, Model AC–21B, 1992.
Chiron, Clemente Optifit Modell SPSP525 Brochure Translation, Dec. 1998.
Chiron Vision, Nuvita MA20, 1997.
Video Tape "New Elliptical Acco. IOL for Cataract Surgery" Shown at ASCRS Symposium on Apr. 10, 1999 (Video Enclosed).
Partial Program Re: ASCRS Symposium, Showing Video Tape shown between Apr. 10–14, 1999.
Jacobi, MD., et al, Arch Ophthalmol, vol. 117, pp. 17–23, Jan., 1999.

* cited by examiner

MULTIFOCAL PHAKIC INTRAOCULAR LENS

BACKGROUND OF THE INVENTION

This invention relates to multifocal intraocular lenses. More particularly, the invention relates to multifocal intraocular lenses adapted for use in a phakic eye, that is in an eye which also includes the natural lens.

Intraocular lenses (IOLs) are commonly used to modify vision. For example, IOLs are used to replace the natural lens of the eye when warranted by medical conditions. A common practice is to implant an IOL in a region of the eye known as the capsular bag or posterior capsule after the natural lens has been removed.

IOLs may be implanted in regions of the eye other than in the capsular bag. For example, monofocal IOLs, that is IOLs which have a single vision correction power, have been implanted in the anterior chamber at the front of the eye, even with the crystalline natural lens remaining in place. In addition, monofocal IOLs have been implanted in the posterior chamber even with the natural crystalline lens being present. Such monofocal IOLs are designed to correct a single vision deficiency, for example, myopia, present in the eye.

Neilsen U.S. Pat. No. 5,158,572 discloses a multifocal intraocular lens useful primarily as a replacement for the natural lens, for example, after a lens extraction operation in which the natural lens is removed. This patent very briefly discloses that the intraocular lens can in some cases be used as an adjunct to the natural lens. However, this patent does not disclose any further special or even specific characteristics of a multifocal intraocular lens used in conjunction with a natural lens as opposed to such a multifocal lens used after natural lens extraction.

Over time, as a human ages, the normal human eye gradually loses the ability to accommodate, that is to focus on objects located at different distances from the eye. This loss of accommodation is generally identified as presbyopia. The natural lens may remain clear and otherwise functional in directing light to the retina of the eye. In this situation, spectacles are often used to correct the presbyopia. In addition, there are varying degrees of presbyopia that are, at least generally, related to the age of the human subject. For example, early stages of presbyopia may occur in individuals in their twenties, and residual accommodation of the natural lens may remain in individuals in their sixties, seventies and beyond. Many people wish to avoid wearing spectacles, particularly in their younger years, to maintain a youthful appearance.

It would be advantageous to provide an intraocular lens adapted for enhanced effectiveness in an eye including a natural lens.

SUMMARY OF THE INVENTION

Intraocular lenses (IOLs) for use in mammalian eyes having natural lenses have been discovered. Such IOLs are particularly useful in phakic eyes in which the natural lens has lost a degree of accommodation or accommodative ability, that is in a partially presbyopic eye. The present IOLs have multiple optic powers, that is are multifocal, preferably having an optic power for each object distance at which an object is formed on the retina. The multifocal design of the lens preferably is mechanically fixed so that the multiple optical powers can operate substantially simultaneously.

An important feature of the present IOLs is that they are configured to take into account the remaining accommodation ability or capability of the natural lens so that enhanced vision is obtained irrespective of the degree of presbyopia present. Put another way, the present IOLs are configured or customized to take into account the specific degree of presbyopia present in the eye in which the IOL is to be implanted. The present IOLs can be made using conventional materials of construction and conventional manufacturing techniques and can be implanted in the eye using procedures which are conventionally employed in implanting other monofocal or multifocal IOLs.

In one broad aspect of the present invention, IOLs are provided for use in mammalian eyes having natural lenses. Such IOLs comprise a lens body sized and adapted for placement in the eye and having a baseline optical power and at least one optical add power, preferably a plurality of different optical add powers. At least one of the optical add powers, preferably each of the add powers, is reduced compared to the baseline optical power of the lens body relative to the corresponding optical power of a similar intraocular lens adapted for placement in a similar eye in which the natural lens has been removed. Such reduced optical add power or powers provide only partial restoration of accommodation. In other words, the reduced optical power or powers of the IOL alone do not provide for full accommodation. However, the reduced optical power or powers of the present IOLs, when combined with the residual natural accommodative ability in the early or partial presbyopic phakic eye, provide enhanced vision, for example, enhanced near vision.

In another broad aspect of the present invention, IOLs are provided for use in mammalian eyes including natural lenses having accommodative capability. The IOLs comprise a lens body sized and adapted for placement in the mammalian eye and having a baseline optical power and at least one optical add power, preferably a plurality of different optical add powers. At least one of the optical add powers, preferably each of the optical add powers of the lens body has a magnitude so that the lens body when placed in the mammalian eye, in combination with the natural lens, provides enhanced vision. This enhanced vision continues as the accommodative capability of the natural lens in the eye decreases. Thus, the magnitude of the add power or powers of the lens body may provide only partial restoration of full accommodation in and of itself. However, when combined with the residual natural accommodative ability in the early presbyope, such IOL provides enhanced vision, for example, enhanced, or even substantially full, near vision or reading vision ability. Even after the early or partial presbyopic subject or presbyope progresses to full or absolute presbyopia, often after more than about five (5) or about ten (10) or about twenty (20) or more years, the reduced add power or powers of the present IOLs provide enhanced vision, for example, at intermediate distances.

The IOLs in accordance with the present invention preferably provide a range of optical powers to allow focusing of distance, intermediate and near images on the retina. In one very useful embodiment the IOL has a simultaneous vision design, that is a concentric and cylindrically symmetric series of zones, such as annular zones, of varying optical power which provide additional or add power for vision at other than distance.

The designed principal optical add power, in particular a near optical power, of the present IOLs preferably is less than the full optical power required for near reading in a pseudophakic subject, that is a subject not having a natural lens in place. This reduced power preferably is less than about 2.5 diopters in the spectacle plane. In a very useful embodiment, the designed principal optical add power of the IOL is reduced, which, in turn, reduces the effects of halos around lights at night while providing acceptable near and/or intermediate vision correction.

The present IOLs preferably provide continuous visual correction or enhancement from distance to near for early (or partial) presbyopes. However, late or absolute presbyopes gradually find a reduction in near vision capabilities employing the present IOLs. Thus, such late, or absolute, presbyopes may require additional vision, e.g., spectacle, assistance for specific near reading tasks. Regardless of the eventual loss of near vision, the additional optical power required for near work is less than that which would be required without the present IOLs. This reduced optical power requirement allows the use of bifocals or progressive spectacles which have fewer field distortions, image jumping and other deleterious visual effects.

The present IOLs may be placed at any position along the optical axis of the eye. For example, the present IOLs can be carried by or secured to the cornea of the eye, for example, such as a corneal implant, e.g., inlay or onlay. Also, the IOLs can be placed posterior of the posterior chamber. The present IOLs may further comprise a fixation member or members coupled to the lens body and adapted to facilitate fixating the IOL in the eye. The fixation member or members preferably are adapted to be placed in the anterior chamber of a mammalian eye or in the posterior chamber of a mammalian eye.

The more likely locations for the present IOLs are in the anterior chamber, for example, with a fixation member or members in the angle of the eye; in the anterior chamber, for example, with a fixation member or members located in contact with the peripheral iris; in the anterior chamber with a fixation member or members located through the iris into the posterior chamber and in contact with the sulcus; or the posterior chamber between the iris and the natural lens with a fixation member or members in contact with the sulcus.

The design of the present IOLS preferably provides that the lens body include a plurality of different regions each having an optical power, for example, a different optical power. The lens body may include a plurality of annular regions each having an optical power and extending radially outwardly from the central axis of the lens body. The lens body preferably is generally circular around the optical axis of the lens body, although other configurations and shapes may be employed and are within the scope of the present invention.

The lens body preferably is configured so that at least one of the optical add powers is reduced by at least about 10%, and more preferably at least about 20% (in terms of diopters from a baseline distance correction optical power) relative to the corresponding optical power of the similar IOL adapted for placement in a similar eye in which a natural lens has been removed. Still more preferably, each of the add powers in the lens body is reduced by at least about 10% and even more preferably at least about 20%, relative to the corresponding optical power of the similar IOL adapted for placement in a similar eye in which the natural lens has been removed.

The present lens bodies preferably are deformable for insertion through a small incision into the mammalian eye. The lens bodies preferably comprise a polymeric material.

In another broad aspect of the present invention, methods for treating presbyopia in a mammalian eye including a natural lens are provided. Such methods provide for placing in the mammalian eye an IOL including a lens body having a baseline optical power and at least one optical add power, preferably, a plurality of different optical add powers, so that the lens body, in cooperation or combination with the natural lens, provides enhanced vision. Intraocular lenses as described herein may be employed in the present methods. The enhanced vision provided by such methods preferably is relative to the vision provided by the mammalian eye without the intraocular lens. The enhanced vision provided preferably is enhanced near vision, particularly in early or partial presbyopes. As noted above, as the subject progresses to full or absolute presbyopia, the enhanced vision provided by the present methods preferably is enhanced intermediate vision.

Each and every feature described herein, and each and every combination of two or more of such features, is included within the scope of the present invention provided that the features included in such a combination are not mutually inconsistent.

These and other aspects of the present invention are apparent in the following detained description and claims, particularly when considered in conjunction with the accompanying drawings in which like parts bear like reference numerals.

DETAILED DESCRIPTION OF THE DRAWINGS

Figure 1:
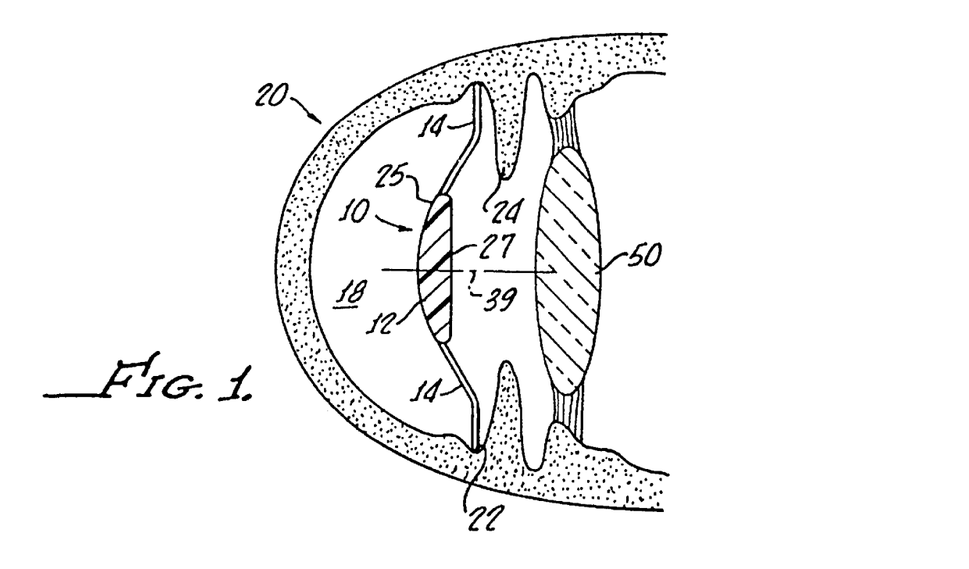
FIG. 1 is a side elevation view of an eye with an anterior chamber intraocular lens in accordance with the present invention implanted therein.
Figure 2:
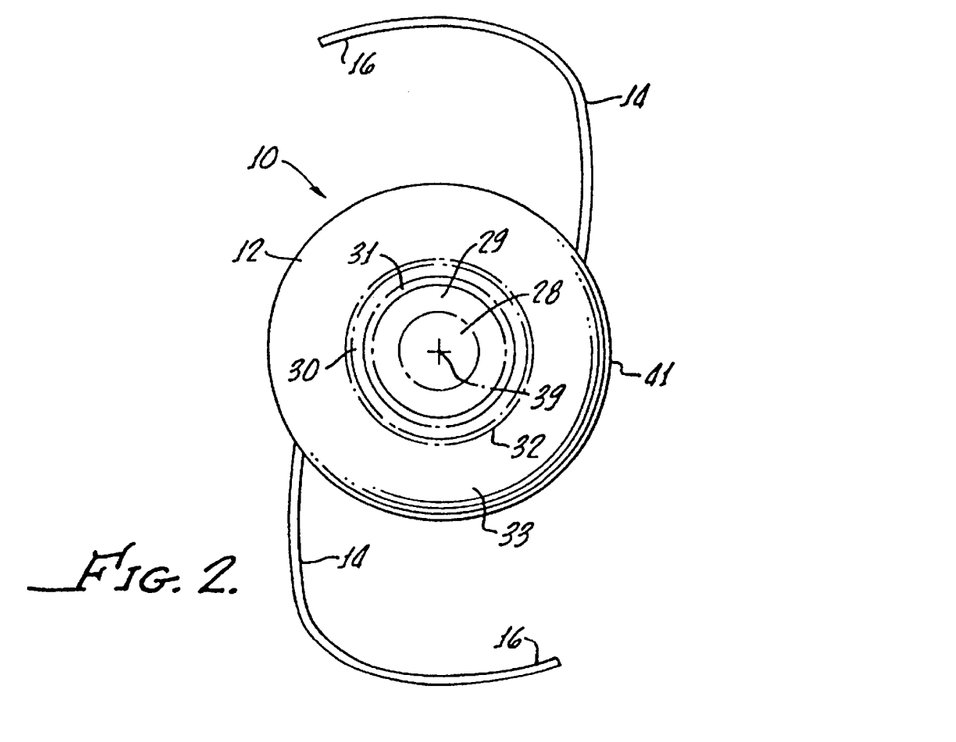
FIG. 2 is a front plan view of the anterior chamber intraocular lens shown in FIG. 1.
Figure 3:
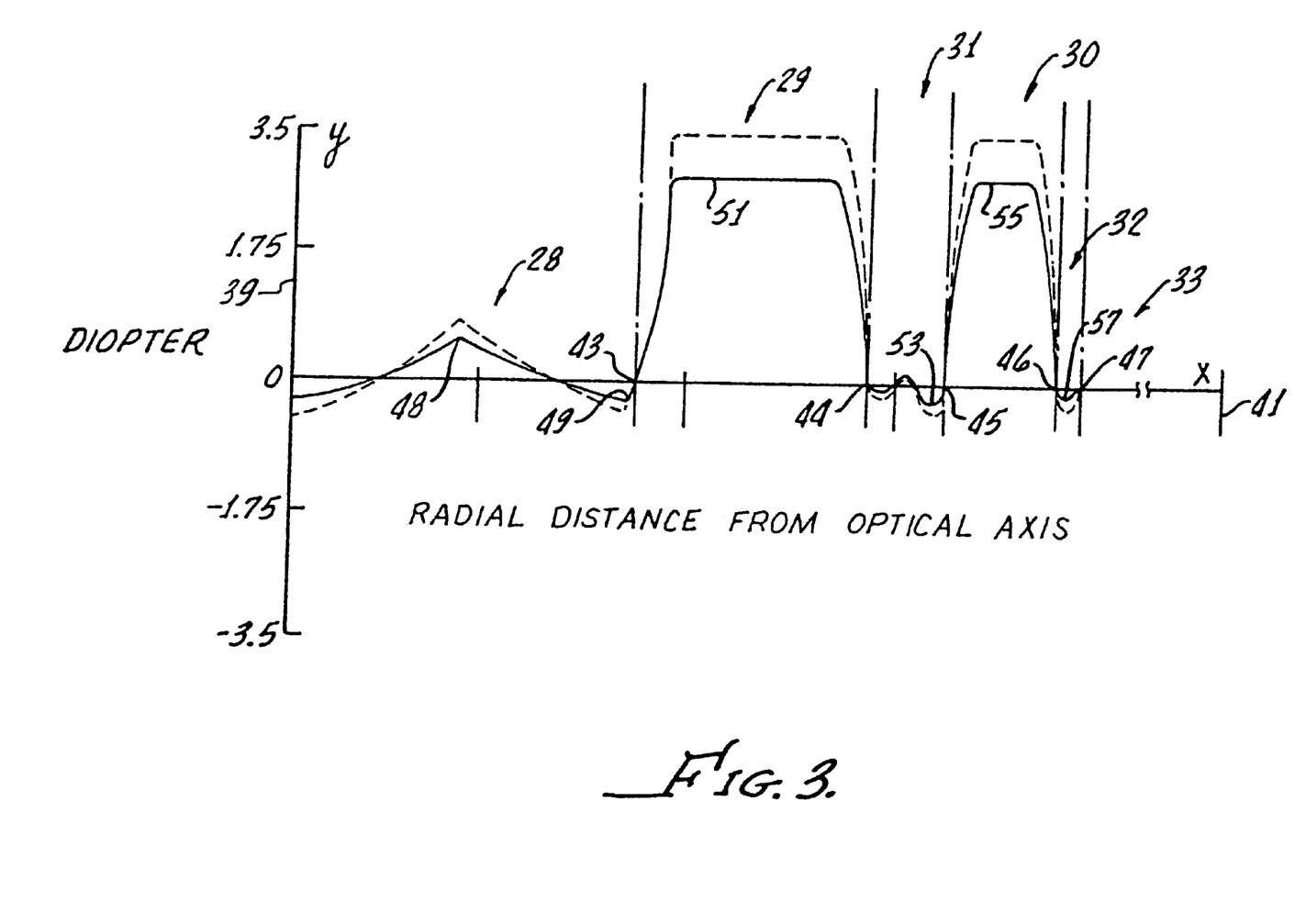
FIG. 3 is a plot of the power of the lens body of the intraocular lens shown in FIG. 1 versus distance from the optical axis of the intraocular lens.

Referring now to FIGS. 1, 2 and 3, an intraocular lens (IOL) according to the present invention, shown generally at 10, includes a multifocal single, unitary lens body 12 having a plurality of optical powers, as described hereinafter. Radially extending fixation members or haptics 14 terminate in distal ends 16. As shown in FIG. 1, intraocular lens 10 is inserted in the anterior chamber 18 of eye 20 with the distal ends 16 of fixation members 14 in contact with the angle 22 of the iris 24.

Any number of configurations can be employed for distal ends 16 of fixation members 14 in order to provide for effective fixation of intraocular lens 10 in anterior chamber 18. However, it is important that the configuration chosen be effective to provide for such fixation while, at the same time, not having an undue detrimental effect on the angle of the anterior chamber or on other components of eye 20. This is particularly true here since the intraocular lens 10 is useful in eyes suffering from the early stages of presbyopia. Thus, the intraocular lens 10 should be designed and configured for long term use, for example, in excess of about ten (10) or about twenty (20) or thirty (30) years or more, in eye 20. Various designs of fixation members have been suggested in the prior art to minimize the detrimental effects of having an intraocular lens in the anterior chamber of the eye.

Such designs may be employed in the present invention to achieve long term effectiveness of the present IOLs with reduced detriment to the eye caused by the presence of the intraocular lens. The fixation members 14 can be made of materials of construction, such as polymeric materials, for example, polypropylene, polymethyl methacrylate and the like, many of which are conventionally used in intraocular lens haptics.

The lens body 12 may be constructed of rigid biocompatible materials such as polymethyl methacrylate (PMMA), or flexible, deformable materials, such as silicone polymeric material, acrylic polymeric material, hydrogel polymeric material and the like, which enable the lens body to be rolled or folded before insertion through a small incision into the eye 20. Although the lens body 12 as shown is a refractive lens body, the present IOLs can include a diffractive lens body and such embodiment is included within the scope of the present invention. In addition, the power curve of lens body 12, seen in FIG. 3, is illustrative, but not limiting, of the present invention. In other words, lens bodies or optics in accordance with the present invention can have any suitable configurations and/or power curves effective to function, for example, to provide one or more benefits, as described herein.

One important aspect of IOL 10 relates to the reduced add power of the optical powers of lens body 12. This can be seen in FIG. 3. The power curve for the lens body 12 is shown as a solid line in FIG. 3. Specifically, the add power or magnitude of the optical power relative to the baseline or "X" axis of FIG. 3 is reduced relative to the add power of a substantially identical lens body, shown in dashed lines in FIG. 3, of a substantially identical IOL adapted for use in an identical eye in which the natural lens has been removed. Thus, the optical power of the lens body 12 remains relatively closer to the baseline power (defined as the "X" axis in FIG. 3) as compared to the optical power of a substantially identical lens body adapted for use in an identical eye in which the natural lens has been removed. Although the amount of reduction in the add power (relative to the above-noted substantially identical lens adapted for use in an identical eye in which the natural lens has been removed) may be as little as about 10% or about 20%, such reduction in the add power is often greater than about 20% and can be in the range of about 30% to about 50% or more.

This reduced add power of lens body 12, particularly with regard to near and/or intermediate vision correction regions, is of substantial importance in the present invention since the natural lens 50 often retains a degree of natural accommodating ability.

Thus, IOL 10 is very effective when inserted into an eye of an early presbyope, that is into the eye of a subject (e.g., human) who suffers a degree of, but not total, presbyopia. The reduced add power of IOL 10 is effective, in combination with the remaining or residual accommodating ability of the natural lens 50, to provide for substantially full accommodation, particularly in the early presbyope in which the loss of accommodating ability is less than about 20% or about 30% or about 50%. The add powers of the lens body 12 are determined, controlled or based, at least in part, by one or more of the following factors: the degree of residual or remaining accommodating ability of the natural lens 50, the age of the subject in whose eye the IOL 10 is to be inserted, the vision needs of the subject, and the expected or anticipated life span of the subject, among other factors many of which are personal to the subject. Thus, the present IOL 10 is often customized to meet the specific and individual needs of the subject in whose eye the IOL 10 is to be inserted.

Thus, for the early or partial presbyope, the lens body 12 provides enhanced vision, particularly for near objects which such early presbyopes often have difficulty in viewing. Such enhanced near vision is provided without the need for spectacles or other vision aids which can have at least a perceived detrimental effect on the appearance of the subject.

Further, even after the natural lens 50 has lost a more substantial portion or even all of its accommodating ability, the IOL 10 continues to provide enhanced vision, for example, enhanced vision in viewing objects at intermediate distances. The later or substantially complete presbyope may require spectacles for viewing near objects. However, the presence of IOL 10 in the eye 20 allows use of bifocals and progressive spectacles which have reduced field distortions, image "jumping" and other detrimental visual effects.

An additional advantage of the reduced add power of IOL 10 is a reduction in the effects of halos around lights, for example, when viewed from a distance, at night.

One particular advantage of the anterior chamber IOL 10 shown in FIG. 1 is that a substantial distance is maintained between the natural lens 50 and the lens body 12. This distance is very effective in providing protection against the IOL 10 touching and possibly harming the natural lens 50.

In the embodiment of FIGS. 1 and 2, the lens body 12 has a convex anterior surface 25 and a planar posterior surface 27; however, these configurations are merely illustrative. Although the vision correction power may be placed on either of the surfaces 25 or 27, in this embodiment, the anterior surface 25 is appropriately shaped to provide the desired vision correction powers.

With particular reference to FIG. 3, the lens body 12 has a central zone 28, inner and outer annular near zones 29 and 30 and annular far zones 31, 32 and 33. In this embodiment, the central zone 28 is circular and the peripheries of the annular zones 29–33 are circular. The annular zones 29–33 circumscribe the central zone 28 and the zones are contiguous. The zones 29–33 are concentric and coaxial with the lens body 12.

The zones 28–33 are used in describing the vision correction power of the lens body 12, and they are arbitrarily defined.

FIG. 3 shows a preferred manner in which the vision correction power of the lens body 12 varies from the center or optical axis 39 of the lens body to the circular outer periphery 41 of the lens body. In FIG. 3, the vertical or "Y" axis represents the variation in diopter power of the lens body 12 from the baseline or far vision correction power, and the "X" or horizontal axis shows the distance outwardly from the optical axis 39, for example, in millimeters. Thus, the zero-diopter or baseline power of FIG. 3 is the power required for far vision for an IOL. The power variation shown in FIG. 3 is applicable to any surface point on lens body 12 at a fixed radial distance from the optical axis 39. In other words, the power at any given radial distance from the optical axis 39 is the same.

The central zone 28 extends from the optical axis 39 to a circular periphery 43, the inner annular near zone 29 is considered as extending from the periphery 43 to a circular periphery 44, and the outer annular near zone is considered as extending from a periphery 45 to a periphery 46. The annular far zone 31 extends between the peripheries 44 and 45, and the annular far zone 32 extends from the periphery 46 radially outwardly to a periphery 47. The annular zone 33 extends from the periphery 47 radially outwardly to the outer periphery 41 of the lens body 22.

The negative diopter powers at the optical axis and the point 49 are of less power than is required for far vision and may be considered as far, far vision correction powers. The actual correction provided by the plurality of optical powers will vary and depends, for example, on the amount of residual accommodative ability present in natural lens 50, among other factors.

The apex 48 has a vision correction power for intermediate vision. The intermediate, far and far, far powers combine to provide a mean power in the central zone 28 for far or distant vision.

Within the inner annular near zone 29, the vision correction power varies from the periphery 43 to a plateau 51, and from the plateau, the vision correction power varies back to the periphery 44 at the baseline. In the far zone 31, the vision correction power increases very slightly above the baseline and then proceeds to a far, far negative vision correction power at a point 53 at which the vision correction power reverses and returns to the baseline at the periphery 45.

In the outer annular near zone 30, the power varies from the periphery 45 to a plateau 55 and returns from the plateau 55 to the baseline at the periphery 46. In the far zone 32, the power dips slightly below the baseline to a point 57 in the far, far correction region and then returns to the baseline at the outer periphery 47. The dips below the baseline to the points 53 and 57 in the far zones 31 and 32 help support an increased depth of the focus of the central zone 28.

The far zone 33 has a vision power that lies along the baseline and is configured for far vision. The entire power curve of lens body 12 from optical axis 39 to outer periphery 41 is shown in FIG. 3, and as shown in FIG. 3 includes no cylinder correction. In other words, as clearly shown in FIG. 3 and as described herein, the power curve of lens body 12 is free of cylinder correction.

Figure 4:
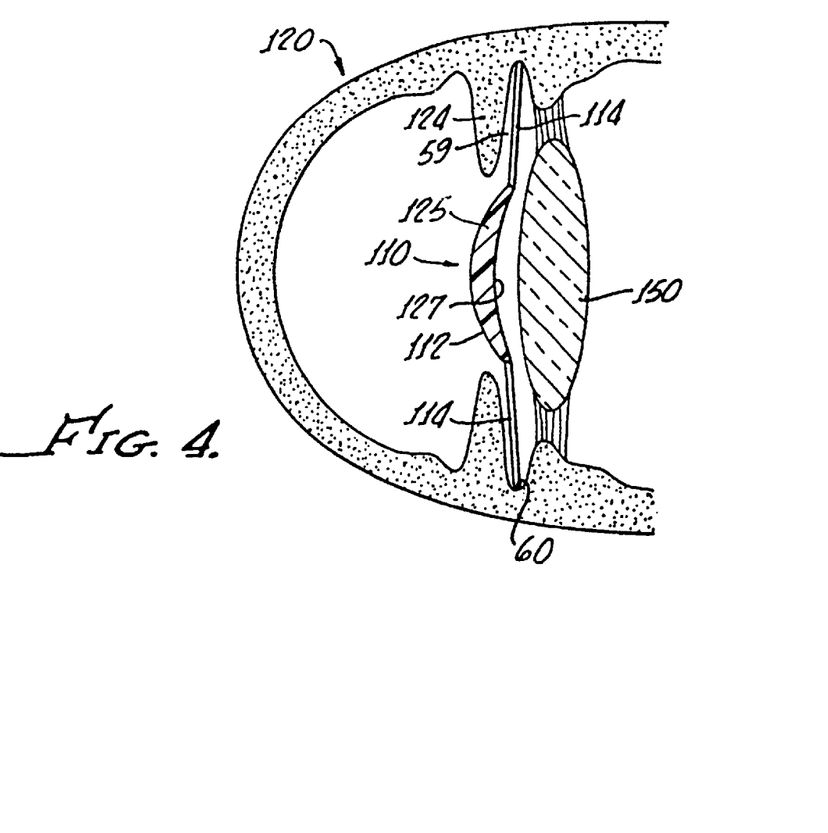
FIG. 4 is a side elavational view of an eye with a posterior intraocular lens in accordance with the present invention implanted therein.
Figure 5:
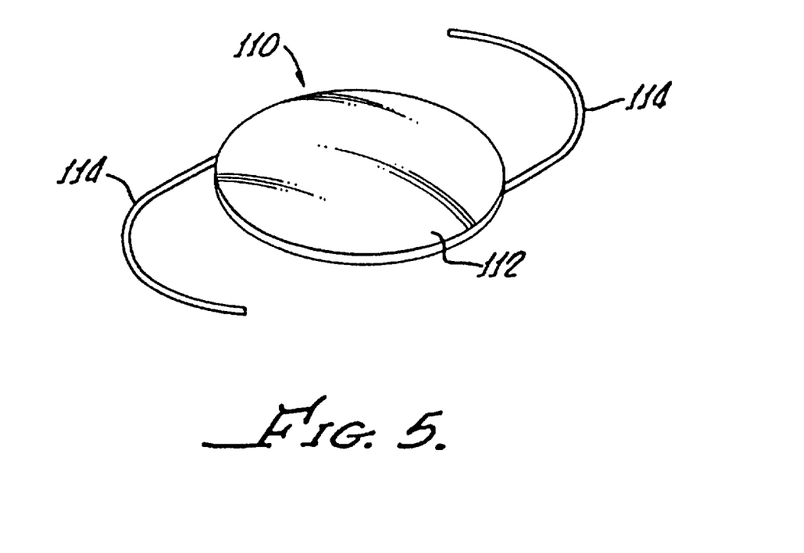
FIG. 5 is a perspective view of the intraocular lens shown in FIG. 4.

An alternate embodiment of an IOL in accordance with the present invention is shown in FIGS. 4 and 5. Except as expressly described herein, this alternate IOL, shown generally at 110, is structured and functions similarly to IOL 10. Components of IOL 110 which correspond to components of IOL 10 are indicated by the same reference numeral increased by 100.

The primary difference between IOL 110 and IOL 10 relates to positioning within the eye. Specifically, IOL 110 is adapted to be placed in the posterior chamber 59, that is behind the iris 124 of eye 120. This is beneficial in that the haptics or fixation members 114 contact the eye at the sulcus 60 which is substantially more resistant to damage than is the angle of the iris in the anterior chamber. Thus, the fixation members 114 are less likely to cause damage to the eye than are the fixation members 14 of IOL 10. This is important since the IOLs in accordance with the present invention are often to be used on a long term basis, e.g., for about twenty (20) or about thirty (30) or more years.

The fixation members 114, because of their placement, may be somewhat different in structure than the fixation members 14.

In addition, as shown best in FIG. 4, the lens body 112 is a convex/concave lens. The concave posterior face 127 is so configured to provide some degree of space between natural lens 150 and lens body 112. Again, it is important that the lens body 112 be spaced apart from the natural lens 150 in order to avoid damaging the natural lens. The multifocal structure of the lens body 112 preferably is present on the convex anterior face 125 of the lens body 112.

IOL 110 performs substantially similarly to IOL 10, to provide enhanced vision both for the early presbyope subject and the subject who is in the later stages of presbyopia or is a substantially full or complete presbyope, as described above.

Figure 6:
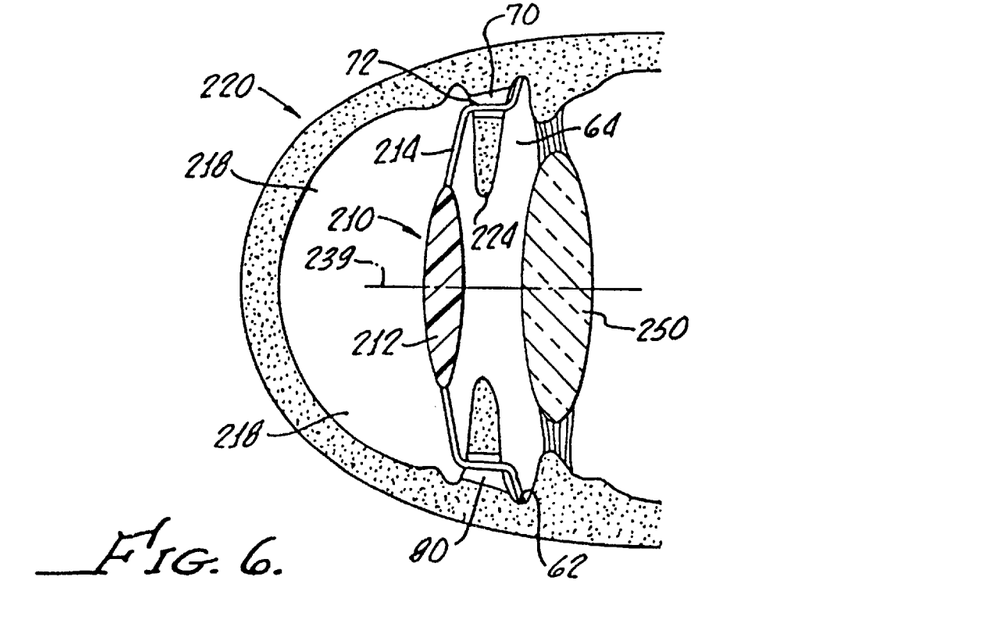
FIG. 6 is a side elevational view of an eye with another embodiment of an intraocular lens in accordance with the present invention implanted therein.
Figure 7:
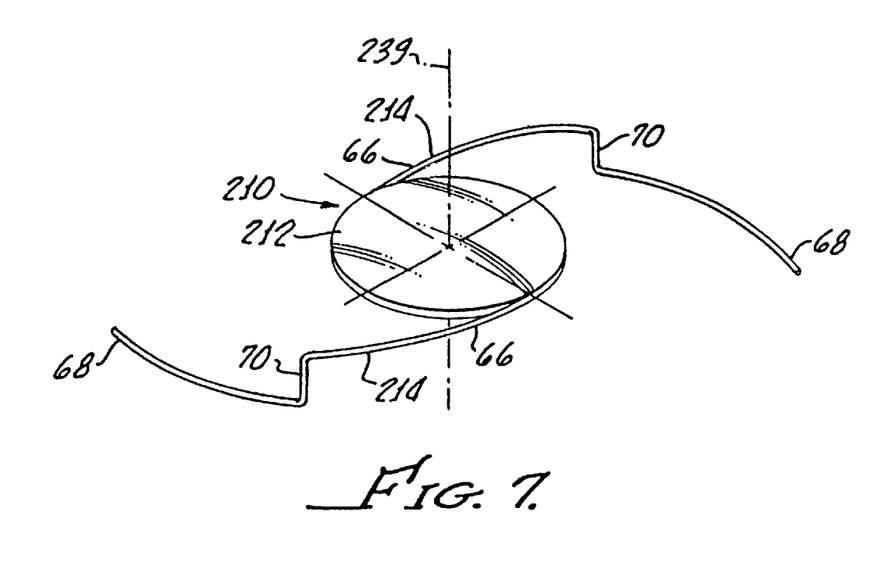
FIG. 7 is a perspective view of the intraocular lens shown in FIG. 6.

FIGS. 6 and 7 show another embodiment of an IOL in accordance with the present invention. Except as expressly described herein, this further embodiment of the present IOLs, shown as 210, is structured and functions similarly to IOL 10. Components of IOL 210 which correspond to components of IOL 10 are indicated by the same reference numeral increased by 200.

In general, the further embodiment of IOL 210 provides that the lens body 212 is located in the anterior chamber but the fixation members are structured so as to contact the sulcus 62 in the posterior chamber 64 of the eye 220. This feature provides for both increased spacing between the lens body 212 and the natural lens 250 and, in addition, allows the fixation members 214 to come in contact with the more sturdy sulcus 62 in fixating the IOL 210 in the eye 220.

FIG. 7 shows IOL 210 comprised of a lens body 212, and two opposing elongated fixation members or haptics 214. Each fixation member 214 has a proximal segment 66 attached to the lens body 212 near the periphery of the lens body. Each fixation member 214 also has a distal segment 68 and an intermediate segment 70 joining the proximal segment 66 and the distal segment 68. The distal segment 68 preferably is more flexible than the other portions of each of the fixation member 214. For example, distal segment 68 can have a reduced cross-sectional area relative to the cross-sectional areas of intermediate segment 70 and proximal segment 66.

The lens body 212 in the shown embodiment is circular in plan and bi-convex.

Each fixation member 214 defines an arc that extends generally normal to the optical axis 239. Each has a discontinuity or a through-iris portion 72 of the intermediate segment 70. The through-iris portion 72 extends generally parallel to the optical axis 239. Other embodiments of the invention may have other suitable arrangements for the fixation members 214 and the through iris portions 72. In the shown embodiment, the haptics 214 are symmetrical. Other embodiments of the invention may have non-symmetrical fixation members. In the shown embodiment of the invention, the fixation members 214 extend generally tangentially away from the lens body. Other embodiments of the invention may have fixation members 214 attached to the lens body 212 which extend in a non-tangential fashion.

The through-iris portions 72 may extend in any suitable direction other than normal to the optical axis 239. In the shown embodiment of the invention, each through-iris portion 72 includes a straight member extending generally parallel to the optical axis 239.

Referring now to FIG. 6, the IOL 210 is shown implanted in the eye 220. Prior to implantation, an iridotomy is performed to form the holes 80 that extend through the iris 224 near the outer periphery of the iris. The iridotomy holes improve fluid flow between the anterior chamber 218 and the posterior chamber 64. The holes 80, as shown, extend through the iris 224 generally parallel to the optical axis 239.

The IOL 210 is implanted such that the lens body 212 and the proximal segments 66 of the fixation members 214 are disposed in the anterior chamber 218. With the lens body 212 in the anterior chamber 218, there is a reduced opportunity for the IOL 210 to contact the natural lens 250 and initiate papillary block and cataract formation. Further, the distal segments 68 of fixation members 214 are disposed in the posterior chamber 64 against the sulcus 62, which reduces the incidence of harm to the angle of the anterior chamber.

Further details of IOLs having fixation members and being positioned in the eye as IOL 210 are provided in commonly assigned U.S. patent application Ser. No. 09/166,328 filed Oct. 5, 1998, the disclosure of which is incorporated herein in its entirety by reference.

IOL 210 performs substantially similarly to IOL 10, to provide enhanced vision both for the early presbyope subject and the subject who is in the later stages of presbyopia or is a substantially full or complete presbyope, as described above.

The present IOLs very effectively provide for enhanced vision for presbyopes whether in the early or partial stages of the condition or in the latter or even substantially complete stages. Thus, because of the reduced powers of the present multifocal lens bodies, the present IOLs can be implanted into an eye having an early or partial form of presbyopia. At this stage, the reduced optical power or powers, in combination with the remaining accommodation ability of the natural lens in the eye, preferably provide for a restoration of full accommodation so that the subject can read and perform other near vision activities without the need for spectacles or other vision aids. As the presbyopia progresses over time with advancing age of the subject, the amount of residual accommodation in the natural lens continues to be reduced. However, the present IOLs are very effective in providing for enhanced vision to the subject, particularly at intermediate distances. At this stage, reading or other near vision activities may require spectacles. Also, because the present IOLs are designed to maintain the eye in good condition and the natural lens in good condition, there is reduced risk that further ocular surgery will be required, for example, to remove the natural lens.

While this invention has been described with respect to various specific examples and embodiments, it is to be understood that the invention is not limited thereto and that it can be variously practiced within the scope of the following claims.

What is claimed is:

1. An intraocular lens for use in a mammalian eye having a natural lens, the intraocular lens comprising:
   a single, unitary lens body sized and structured for placement in the eye, spaced apart from the natural lens of the eye, and having a baseline optical power, a first optical add power for near vision, and a second optical add power intermediate between the first optical power and the baseline optical power, the first optical add power is reduced relative to the corresponding optical power of a substantially identical intraocular lens adapted for placement in an identical eye in which the natural lens has been removed, the lens body includes a plurality of different regions each having a different add power, and is free of cylinder correction.

2. The intraocular lens of claim 1 wherein the lens body includes a plurality of different optical add powers, each of the different optical add powers being reduced relative to the corresponding optical power of a substantially identical intraocular lens adapted for placement in an identical eye in which the natural lens has been removed.

3. The intraocular lens of claim 1 which further comprises a fixation member coupled to the lens body and adapted to facilitate fixating the intraocular lens in the eye.

4. The intraocular lens of claim 3 wherein the fixation member is adapted to be placed in an anterior chamber of the eye.

5. The intraocular lens of claim 3 wherein the fixation member is adapted to be placed in a posterior chamber of the eye.

6. The intraocular lens of claim 1 wherein the lens body is sized and structured for placement in an anterior chamber of a human eye.

7. The intraocular lens of claim 1 wherein the first optical add power is reduced by at least about 10% relative to the corresponding optical power of a substantially identical intraocular lens adapted for placement in an identical eye in which the natural lens has been removed.

8. The intraocular lens of claim 1 wherein the lens body is adapted to be placed in an anterior chamber of the eye.

9. The intraocular lens of claim 1 wherein the lens body is adapted to be placed in a posterior chamber of the eye.

10. The intraocular lens of claim 1 wherein the lens body is deformable for insertion through a small incision into the eye.

11. An intraocular lens for use in a mammalian eye including a natural lens having an accommodative capability, the intraocular lens comprising:
    a single, unitary lens body sized and structured for placement in the mammalian eye, spaced apart from the natural lens, and having a baseline optical power, a first optical add power including a near vision optical power and a second optical add power intermediate between the first optical add power and the baseline diopter power, the first optical add power having a magnitude so that the lens body when placed in the mammalian eye, in combination with the natural lens, provides enhanced vision, the lens body is free of cylinder correction.

12. The intraocular lens of claim 11 which further comprises a fixation member coupled to the lens body and adapted to facilitate fixating the intraocular lens in the eye.

13. The intraocular lens of claims 12 wherein the fixation member is adapted to be placed in an anterior chamber of the eye.

14. The intraocular lens of claim 12 wherein the fixation member is adapted to be placed inca posterior chamber of the eye.

15. The intraocular lens of claim 11 wherein the first optical add power has a magnitude which is reduced to take account of the accommodation capability of the natural lens.

16. The intraocular lens of claim 11 wherein the lens body is sized and structured for placement in an anterior chamber of a human eye.

17. The intraocular lens of claim 11 wherein the lens body is adapted to be placed in an anterior chamber of the eye.

18. The intraocular lens of claim 11 wherein the lens body is adapted to be placed in a posterior chamber of the eye.

19. The intraocular lens of claim 11 wherein the lens body is deformable for insertion through a small incision into the eye.

20. A method for treating presbyopia in a mammalian eye including a natural lens, the method comprising:
    placing in the eye, spaced apart from the natural lens of the eye, an intraocular lens including a single, unitary lens body having a baseline optical power, a first optical add power having a magnitude which is reduced to take account of the accommodation capability of the natural lens and a second optical add power intermediate between the first optical add power and the baseline optical power so that the lens body, in cooperation with the natural lens, provides enhanced vision, the lens body is free of cylinder correction.

21. The method of claim 20 wherein the eye includes an anterior chamber, the lens body is placed in the anterior chamber, and the enhanced vision provided is relative to the vision provided by the eye without the intraocular lens.

22. The method of claim 20 wherein the first optical add power is reduced relative to the corresponding optical power of a substantially identical intraocular lens adapted for placement in an identical eye in which the natural lens has been removed.

23. An intraocular lens for improving the vision of a patient comprising:

a single, unitary multifocal lens body sized and structured for placement in an eye and having a plurality of optical powers including a baseline optical power, a maximum optical add power less than the optical add power required for full near vision correction, and an additional optical add power intermediate between the maximum optical add power and the baseline optical power, the lens body includes a plurality of regions for enhancing near vision and is free of cylinder correction.

24. The intraocular lens of claim 23 wherein the lens body includes at least one region for enhancing intermediate vision.

25. The intraocular lens of claim 23 wherein the optical add power of at least one of the plurality of regions for enhancing near vision has a maximum optical add power which is at least about 10% less than the optical add power required for full near vision correction.

26. The intraocular lens of claim 23 wherein the optical add power of at least one of the plurality of regions for enhancing near vision has a maximum optical add power which is at least about 20% less than the optical add power required for full near vision correction.

27. The intraocular lens of claim 23 wherein the optical add power of at least one of the plurality of regions for enhancing near vision has a maximum optical add power which is at least about 30% less than the optical add power required for full near vision correction.

28. The intraocular lens of claim 23 wherein the optical add power of at least one of the plurality of regions for enhancing near vision has a maximum optical add power which is at least about 50% less than the optical add power required for full near vision correction.

29. The intraocular lens of claim 23 wherein the lens body is sized and structured for placement in an anterior chamber of a human eye.

30. An intraocular lens for use with an eye of a patient comprising a single, unitary multifocal lens body having an optical axis and an optical power which changes along a power curve in a radially outward direction from the optical axis, the lens body having a baseline optical power, a maximum optical add power and an additional optical add power intermediate between the maximum optical add power and the baseline optical power, the maximum optical add power being less than the optical add power required for full near vision correction, the lens body includes a plurality of regions for enhancing near vision and is free of cylinder correction.

31. The intraocular lens of claim 30 wherein the lens body includes at least one region for enhancing intermediate vision.

32. The intraocular lens of claim 30 wherein the optical add power of at least one of the plurality of regions for enhancing near vision has a maximum optical add power which is at least about 10% less than the optical add power required for full near vision correction.

33. The intraocular lens of claim 30 wherein the optical add power of at least one of the plurality of regions for enhancing near vision has a maximum optical add power which is at least about 20% less than the optical add power required for full near vision correction.

34. The intraocular lens of claim 30 wherein the optical add power of at least one of the plurality of regions for enhancing near vision has a maximum optical add power which is at least about 30% less than the optical add power required for full near vision correction.

35. The intraocular lens of claim 30 wherein the optical add power of at least one of the plurality of regions for enhancing near vision has a maximum optical add power which is at least about 50% less than the optical add power required for full near vision correction.

36. The intraocular lens of claim 30 wherein the lens body is sized and structured for placement in an anterior chamber of a human eye.

* * * * *